(12) United States Patent
Meijs et al.

(10) Patent No.: US 8,709,440 B2
(45) Date of Patent: Apr. 29, 2014

(54) AGENT FOR EXPELLING PARASITES IN HUMANS, ANIMALS OR BIRDS

(75) Inventors: Maria Wilhemina Meijs, Lanaken (BE); Jan Jozef Vaessen, Lanaken (BE)

(73) Assignee: Momentum Animal Cure BVBA, Lanaken (BE)

( * ) Notice: Subject to any disclaimer, the term of this patent is extended or adjusted under 35 U.S.C. 154(b) by 0 days.

(21) Appl. No.: 13/463,014

(22) Filed: May 3, 2012

(65) Prior Publication Data

US 2012/0231032 A1    Sep. 13, 2012

Related U.S. Application Data

(63) Continuation-in-part of application No. PCT/BE2010/000077, filed on Nov. 5, 2010.

(30) Foreign Application Priority Data

Nov. 6, 2009   (BE) .................................. 2009/0689

(51) Int. Cl.
*A61K 31/00* (2006.01)
*A61K 35/00* (2006.01)
*A61K 36/00* (2006.01)

(52) U.S. Cl.
USPC .................................................... 424/195.18

(58) Field of Classification Search
None
See application file for complete search history.

(56) References Cited

PUBLICATIONS

HG/518. "1le3/4maailendrarasaa" from Nityancthansiddha Rasranekara-Rasendra kha2am Comm Datto Ballel Borokara, Ed. 2$^{nd}$ (1986) Sri Gajenan Book Depot, Pune, pp. 662-664. Retrieved from TKDL database on Jun. 17, 2013 online.*

Mahendra Bhaugika, Dhanvantarinighantauh, p. 04-08, Edn. 3rd, 2002, Chaukhambha Orientalia, Varanasi, UP, India.
Mohammad Azam Khan, Ikseer Azam, vol. 111, p. 09-12, 1917 AD, Munshi Nawal Kishore, Lucknow, UP, India.
Mohammad Akmal Khan, Ikseer Azam, vol. III, p. 13-17, 1917 AD, Munshi Nawal Kishore, Lucknow, UP, India.
J. Blancou, et al., Historical and Anecdotal Activity Regarding Ancient Plant Therapy of Infectious and Parasitic Animal Diseases, Phytotherapie (2006) vol. 5, No. 2, p. 74-82.
Zahid Farooq, et al., Ethnoveterinary Practices for the Treatment of Parasitic Diseases in Livestock in Cholistan Desert (Pakistan) Journal of Ethnopharmacology (2008) vol. 118, p. 213-219.
Mradu Gupta, et al., Therapeutic Utilization of Secretory Products of Some Indian Medicinal Plants—A Review, Indian Journal of Traditional Knowledge, Resources, New Delhi, India (2006) vol. 5, No. 4, p. 569-575.
Abdul Jabbar, et al., An Inventory of the Ethnobotanicals Used as Anthelmintics in The Southern Punjab (Pakistan), Journal of Ethnopharmacology (2006) vol. 108, p. 152-154.
Pradeep Kumar, et al., Molluscicidal Activity of *Ferula asafoetida*, *Syzygium aromaticum* and *Carum carvi* and Their Active Components Against the Snail *Lymnaea acuminata*, Chemosphere (2006) vol. 63, No. 1568-1574.
Medline/NLM Accession No. 15658063: Ramadan Nashwa, et al., Effect of *Ferula assafoetida* on Experimental Murine Schistosoma Mansoni Infection; Journal of Egyptian Society of Parasitology (2004) vol. 34.
Shalini Nagaich, et al., Anthelmintic Efficacy of the Aqueous Extract of *Ferula asafoetida* (Vern. Heing) Against Common Poultry Worms *Ascaridia galli* and *Heterakis gallinae*, J. Parasit. Appl. Anim. Biol. (Jan.- Jul. 2001) vol. 10, Nos. 1&2, p. 83-88.
Nashwa I. Ramadan, et al., The In Vitro Effect of Assafoetida on *Trichomonas vaginalis*, Journal of Egyptian Society of Parasitology (2003) vol. 33, No. 2, p. 615-630.

* cited by examiner

*Primary Examiner* — Amy L Clark
(74) *Attorney, Agent, or Firm* — Vedder Price P.C.; Thomas J. Kowalski; Deborah L. Lu

(57) ABSTRACT

This invention relates to an agent which may be used to expel parasites from humans, mammals or birds. The agent of the invention may a vegetable product, *Ferula Assafoetida*, which is very effective in expelling parasites.

25 Claims, 3 Drawing Sheets

AGENT FOR EXPELLING PARASITES IN HUMANS, ANIMALS OR BIRDS

RELATED APPLICATIONS AND INCORPORATION BY REFERENCE

This application is a continuation-in-part application of international patent application Serial No. PCT/BE2010/000077 filed 5 Nov. 2010, which published as PCT Publication No. WO 2011/054066 on 12 May 2011, which claims benefit of Belgium patent application Serial No. 2009/0689 filed 6 Nov. 2009.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to a substance which can be used for expelling and preventing the occurrence of parasites, from humans, mammals or birds.

BACKGROUND OF THE INVENTION

Parasites are life-forms which sustain themselves and reproduce at the expense of another organism, the host. They comprise endoparasites and ectoparasites. Parasitic worms or helminths which live inside their host feed themselves via the living host and in this way gain protection while the food absorption of the host is impaired, whereby it becomes weak and ill. The consequences of parasite infections are generally known. They cause gastroenteritis, diarrhoea, serious weight loss, colic and other disorders, sometimes resulting in death.

The endoparasites comprise parasites living inside the gastrointestinal, or in other organs, such as liver, and lungs. Ectoparasites live on the surface of the host.

They occur in humans as well as animals. Parasitic worms include the platyhelminths or flatworms, to which the cestodes or the tapeworms and the trematodes, such as liver fluke, belong, and the nematodes or the roundworms. Cestodes are segmented flatworms, trematodes are unsegmented flatworms and nematodes are cylindrical worms.

Other types of parasites that live inside the gastrointestinal tract are parasitic arthropods such as larvae of flies and mites, and protozoa. A large number of anthelmintics are already commercially available. However, the helminths develop an increasing resistance to most of the known anthelmintics. Resistance is highly disadvantageous since it results in the reduction of reproduction in livestock, other mammals and birds, and additionally results in a threat to the success of present treatment.

There are various causes for the occurrence of resistance. Resistance can inter alia occur due to changes in genes or in gene expressions, whereby the medicine can react or be modified, resulting in the loss of the activity and the survival of the helminths.

Resistance mechanisms can also occur due to the involvement of transport proteins which remove the medicines such that the medicine can no longer reach their target.

There are several reasons which lead to these resistance mechanisms. This can be due to a treatment frequency which is too high, repetitive use of the same medication regimes, or under dosing the anthelmintics. Public health authorities rely increasingly on mass medication administration programs to control parasites in both humans and animals such as livestock. They are however aware that resistance to medication can always increase and are searching for other options. In the Netherlands for instance a chemical anthelminthic for horses is still available only on veterinary prescription. The purpose here is to avoid excessive use and to avoid the occurrence of faster increasing resistance. In addition, the amount of antiparasitic medicines on the market is limited, and only a small number of new medicines are being developed.

For each chemical class of anthelmintics (imidothiazole, benzimidazole, macrocyclic lactones and others) it is the case that a resistance to one type of medicine generally brings about resistance to other types. It is possible, and is also an increasingly frequent occurrence, that there are multiple resistances wherein parasites develop sequential resistance, this irrespective of determined classes of anthelmintics. Furthermore, once a parasite is resistant to a determined population of medicines, it has never yet been the case that this population loses its resistance. When an anthelmintic class is first administered, there are only a few resistance alleles. This indicates that, if there is no treatment, resistance alleles carry with them neutral or negative reproduction fitness. Resistance is moreover an inevitable consequence of the use of medicines and the selection for resistance would depend on the relative reproduction rate assigned to the susceptibility of resistance alleles to a determined level of use of medicines.

For specific parasites and in specific situations of medicine use it may be that resistance never develops. When resistance to a medicine occurs, there are three stages linked to the accumulation of resistance alleles:

1. Resistance is generally a random event influenced by the population size and diversity; mutation rate of the genes; and the relative condition of those individuals having the mutation compared to the wild-type gene. The frequency of the resistance allele is in general fairly low.
2. The development of the resistance occurs as a response to a selective agent which kills susceptible worms but which allows those which are resistant to survive and reproduce. Treatment with the medicines is therefore a very potent means for selecting resistance alleles. If continuous selection takes place, the frequency of the resistance alleles then increases and these are spread through the population.
3. Resistance develops as soon as the selection increases progressively and increasing numbers of R-alleles occur. From this moment the parasite is found to have become resistant.

The presence of resistant genotypes always occurs much faster than clinical resistance can be observed. Since the medicines are very often used in a dosage which is much higher than the minimum required to kill most of the worms, the selection can produce a high frequency of R-alleles before clinical resistance is observed.

Due to the fast increasing resistances occurring in helminth that is developed against a known chemical class of anthelminthics, there is a need for a new substance, which acts in a different way and belongs to another class of medicines, for combating parasites in animals as well as humans.

Citation or identification of any document in this application is not an admission that such document is available as prior art to the present invention.

SUMMARY OF THE INVENTION

Accordingly, it is an object of the present invention amongst other objects, to provide a new substance for use in expelling parasites which is effective, easy to prepare and simple to administer. Further, another object of the present invention is to provide a vegetable product (or phytotherapeutic agent) for expelling parasites in a natural and effective manner while it is nevertheless well tolerated by the digestive system and limited or no side-effects occur.

Yet another object of the present invention is to prevent harmful effects on the environment. It has after all been found that chemical anthelminthics used at this moment enter the faeces on the land and have a harmful effect on insects, whereby the insects die.

Furthermore, it is an object of the invention to provide increased efficacy in expelling parasites compared to the known chemical anthelminthics.

The above objects, amongst other objects, are met at least partially, if not completely by a Ferula assafoetida (asafoetida) for use in expelling parasites, wherein the parasites are endoparasites in domestic animals, Equus or Suidae; human digestive tract endoparasites; or ectoparasites in humans, mammals or birds.

Especially, the above objects, amongst other objects, are met at least partially if not completely by asafoetida.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 1A depicts one cat was infected with parasites. After treating the cat with 0.3 g asafoetida resin, the cat gained weight and lost its parasites (FIG. 1B).

DETAILED DESCRIPTION OF THE INVENTION

Figure 1A:
FIGS. 1A-1B depict the effect of asafoetida resin on an infected cat.

The present inventors have surprisingly found that Asafoetida can be used for expelling parasites, whereby the parasites are ectoparasites and endoparasites, from humans, mammals or birds. Further, the inventors have found that Asafoetida can be used for preventing the occurrence of parasites, whereby the parasites are ectoparasites and endoparasites, form humans, mammals or birds.

Furthermore, the inventors have found that Asafoetida is an effective substance in expelling parasites, or preventing occurrence of parasites, from animals that are infected with parasites that are resistant to other substances that expel parasites that are not resistant.

As used herein, the term "endoparasites" is intended to denote parasites, comprising helminths and protozoa, which occur inside a living organism. These comprise the intestinal parasites, which occur in the digestive tract, liver fluke and lungworms. They further comprise protozoa and parasitic arthropods such as larvae of mites and flies. The term "ectoparasites" is intended to denote parasites living on the surface of the hosts. They comprise arthropods and helminths.

According to this invention, helminths comprise cestodes, trematodes or nematodes.

As used herein, resistance means when a determined dosage or concentration of a constituent generally has an effect on a large number of individuals in a parasite population, and this concentration no longer has an effect, or a larger concentration of the medicine is required to achieve a determined level of efficacy.

Asafoetida (Ferula assafoetida) is a plant belonging to the family of the Umbelliferae (or the Apiaceae), or the umbellifer family. Asafoetida is a herb originally from Persia which is often used in India. It has a very strong penetratingly unpleasant smell and is used in small quantities in particular dishes. Asafoetida also appears to be a traditional remedy for chronic bronchitis and flatulence.

It has been found that asafoetida has an increased efficacy in expelling parasites. Expelling parasites denotes combating, stunning and/or killing parasites. Whole, broken or cut asafoetida, parts of the plant such as the leaves, flowers, stalks and roots can be used for this purpose in dried or fresh form.

It has been found that asafoetida expels parasites from infected animals by applying the compound only one time. Another embodiment of the invention is Asafoetida or a preparation of asafoetida for expelling parasites, by administering asafoetida one time to the animal, or the person infected with parasites.

It has been found that asafoetida shows efficacy after a short time. It has been found that asafoetida has an expelling effect after two-seven days.

According to another aspect, the invention relates to a preparation of *Ferula assafoetida* (asafoetida) or a composition thereof, further comprising a therapeutically acceptable agent or excipient. The preparation of asafoetida can be obtained by extraction, distillation, pressing, fractionation, purification, concentration or fermentation. Examples are ground or powdered substances of asafoetida, tinctures, extracts, essential oils, pressed juices. The preparation can comprise phenols, polyphenols, terpenoids, sesquiterpenes, alkaloids, lectin polypeptides, mixtures hereof or derivatives hereof, and so on. The method for preparing and processing preparations is generally known by the skilled person and the preparations can be prepared from roots, flowers, leaves and stalks of the plant. The preparation comprises the active constituent which expels the helminths from the mammals, humans or birds. It is possible that, by making use of the preparation comprising the active constituent, the smell wholly or partially disappears, whereby administering to mammals becomes easier because they are no longer put off by the smell of asafoetida.

In a preferred embodiment, the preparation of Asafoetida is a resin made from the plant. The resin can come from the dried sap extracted from the stem and roots of the Asafoetida plant. The resin is greyish-white when fresh, but dries to a dark amber colour.

In another preferred embodiment, the preparation of Asafoetida is a powder form. The powder of asafoetida can also be mixed with Arabic gum. The mixture can for example have about 30-100 wt % of asafoetida and 70-0 wt % Arabic gum and has preferably a ratio between about 60 wt % Asafoetida and 40% Arabic gum.

In another aspect of the invention *Ferula assafoetida* (asafoetida) or a preparation of *Ferula asafoetida* is used for expelling parasites, such as an anthelminthic, wherein the parasites are resistant to a compound that has an parasite expelling effect, such as an anthelminthic activity, against parasites that are not-resistant. Or in other words asafoetida or a preparation thereof shows efficacy where another substance generally has an effect on a parasite population, and this substance has no longer an effect. Or, yet in other words, Asafoetida or a preparation thereof, expels parasites, such as helminths, that are resistant to other compounds that expel parasites, such as chemical anthelmintics.

Examples of other compounds that expel parasites, and whereby it is known that parasites have developed resistance to these compounds, are the anthelmintics, comprising benzimidazoles such as thiabendazole, mebendazole, fenbendazole, oxibendazole, fenbendazole, oxfendazole, febantel and albendazole; macrocyclic lactones such as ivermectin, abamectin, doramectin, eprinomectin, moxidectin; imidothiazoles such as levamisole, and others such as netobimin, morantel, diethylcarbamazine, niclosamide, praziquantel, pyrantel pamoate, piperazine citrate, flubendazole, piperazine adipate, milbemycin oxime, imidacloprid, emodepside, closantel, levamisole hydrochloride, or a constituent derived therefrom. Resistant strains of parasites against the other anthelmintics are known in the art. In one embodiment of the invention asafoetida or a preparation thereof is used in mammals infected with parasites, or with parasites that are resistant to a compound that has an parasite expelling effect, against parasites that are not-resistant, where the mammals belong to the Bovinae family, and more particularly Bovinae *Bos* or cattle; *Ovis*, and more particularly *Ovis aries* or sheep; the Capra family, and more particularly Capra *aegagrus hircus* or the goats or Suidae, and more particularly Suinae *sus*, or pigs.

The treatment of livestock in general, and cattle, sheep and goats in particular, is very important for the meat industry and animal feed industry. The sale of meat is subject to strict standards and it is undesirable for these animals to be infected with parasites. In addition, parasites can soon weaken livestock, whereby the milk production deteriorates and the production of offspring is also made more difficult. Asafoetida is a constituent which can expel the parasites and prevent these problems.

In another embodiment of the invention, asafoetida or a preparation thereof is used in mammals infected with parasites, or with parasites that are resistant to a compound that has an parasite expelling effect, against parasites that are not-resistant, where the mammals are domestic pets and zoo animals, belonging to the group family Canis, and more particularly Canis *lupus familiaris* or the dog; the family Filinae, and more particularly *Felis catus* or the domestic cat; the Leporidae family and more particularly rabbits or *Oryctolagus cuniculus*; the Cricetidae family and more particularly the hamster or *Cricetus cricetus*; and the Caviidae family, and more particularly the cavia which can be treated against parasites with asafoetida or a preparation thereof. Domestic pets come into close contact with humans and their share is becoming increasingly important. It is therefore of great importance that these animals can be treated in a simple manner for parasites. Recent studies revealed that about 14% of the US population is infected with Toxocara worms. These types of worms can be passed from animal to human. It is important that pets, such as cats and dogs, can be dewormed on a fast and effective way.

Asafoetida is therefore very suitable for this purpose and can thus contribute toward preventing transfer of parasites from domestic animals to humans.

In another preferred embodiment of the invention, asafoetida or a preparation thereof is used in the Equus family infected with parasites, or with parasites that are resistant to a compound that has a parasite expelling effect, against parasites that are not-resistant, where the Equus are zebras, and more particularly Equus *ferus caballus* or horses and ponies. Horses are very valuable animals which are very useful to humans. It is very important for horses to remain fit. Finding a good treatment for horses is not a matter of course. This is because a horse has a very delicate digestive system. The horse has a very strong cut-off valve muscle for the stomach and cannot vomit. Horses are hereby very selective in their food take-up. Via their sense of smell horses can distinguish well which feed may and may not be eaten. This is in contrast to ruminants (including cattle, goats and sheep), and herbivores, which when the stomach is full allow the food to return to the mouth and chew the cud. The digestive system of a horse can withstand the digestion of raw cellulose due to the presence of a well-developed caecum (and large intestine). A horse has only one stomach for the purpose of digesting feed, in contrast to the ruminants which have four stomachs. The stomach of the horse is also very small in relation to its size; the size of the stomach of the horse is similar to the stomach of a large dog. The horse has a very extensive intestinal system in which blockages can easily occur. A horse is therefore extra-sensitive and it is not easy to find a plant or active constituent which can expel parasites which also works with horses. Horses are also very sensitive to specific herbs, including ragwort (*Senecio jacobea* L.) and buttercup, which are toxic and can cause death after excessive consumption. It is very surprising that Asafoetida, and more particularly a preparation of asafoetida in the form of resin, expels the parasites from horses and thereby has no adverse consequences for the animal.

In another embodiment of the invention asafoetida or a preparation thereof is used in a bird or Ava infected with parasites, or with parasites that are resistant to a compound that has an parasite expelling effect, against parasites that are not-resistant, wherein the birds are in particularly poultry (chickens, turkey, guinea fowl, goose, duck, ostrich and emu), pigeons (Columbidae), and exotic birds and cage-birds (including psittacines or *Psittaciformes*, or canary *Serinus canaria* and other passerines—Fringillidae, pheasants, quails, tragopans, partridges, peacocks, guinea fowl, francolins). Birds are also very important to humans, both in the food industry and poultry industry, as well as for sport (including pigeons) and as hobby and as animal companion. It is therefore also extremely important for these animals that they can be treated for parasites.

In another embodiment of the invention asafoetida or a preparation thereof can combat one or more parasites, or parasites that are resistant to a compound that has a parasite expelling effect, against parasites that are not-resistant, where the parasites are endoparasites belonging to the group selected from flatworms including the cestodes or tapeworms; trematodes including liver fluke (Fasciola hepatica); roundworms or nematodes including the gastrointestinal nematodes such as Ascaris, lungworms, hookworms and mine worms; arthropods such as larvae of flies or mites, present in the intestinal system; or Protozoa such as *Cryptosporidium parvum, Eimeria, Giardia duodenalis, Histomonas meleagridis, Neospora caninum* and *Toxoplasma gondii*; or are ectoparasites comprising mites, flies, lice, fleas or ticks.

In another embodiment of the invention asafoetida or a preparation thereof can combat one or more parasites, or parasites that are resistant to a compound that has a parasite expelling effect, against parasites that are not-resistant, where the parasites occur in Equus and are selected from the group consisting of *Anaplocephala perfoliata, Anaplocephala* spp., *Ascaris* spp., *Cilicodontophorus bicornatus, Cilicodontophorus* spp., *Cilicostephanus asymetricus, Cilicostephanus bidentatus, Cilicostephanus calicatus, Cilicostephanus goldi, Cilicostephanus longibursatus, Cilicostephanus minutes, Cilicostephanus* spp., *Coronocyclus coronatus, Coronocyclus labiatus, Coronocyclus labratus, Coronocyclus* spp., *Craterostomum acuticaudatum, Craterostomum* spp., *Cyathostomum catinatum, Cyathostomum pateratum, Cyathostomum* spp., *Cylicocereus* spp., *Cylicocyclus ashworthi, Cylicocyclus brevicapsulatus, Cylicocyclus elongates, Cylicocyclus insigne, Cylicocyclus leptostomum, Cylicocyclus nassatus, Cylicocyclus radiates, Cylicocyclus* spp., *Cylicocyclus ultrajentinus, Cylicodontophorus bicoronatus, Cylicodontophorus* spp., *Cylicostephanus* spp., *Dictyocaulus arnfieldi, Dictyocaulus* spp., *Fasciola hepatica/gigantic, Gasterophilus intestinalis, Gasterophilus nasalis, Gasterophilus* spp., *Gyalocephalus capitatus, Gyalocephalus* spp., *Habronema muscae, Habronema* spp., *Onchocerca* spp., *Onchocerca cervicalis, Oxyuris equi, Oxyuris* spp., *Paranoplocephala mamillana, Paranoplocephala* spp., *Parapoteriostomum mettami, Parapoteriostomum* spp., *Parascaris equorum, Parascaris viviparum, Parascaris* spp., *Petrovinema poculatus, Petrovinema* spp., *Poteriostomum imparidentatum, Poteriostomum* spp., *Strongylus edentates, Strongyloides westeri, Strongylus craterostomum, Strongyloides* spp., *Strongylus edentatus, Strongylus equinus, Strongylus* spp., *Strongylus triodontophorus, Strongylus vulgaris, Trichonema* spp., *Trichostrongylus axei, Trichostrongylus* spp., *Triodontophorus brevicauda, Triodontophorus serratus, Triodontophorus* spp., *Triodontophorus tenuicollis, Paramphistomum* spp., *Paramphistomum cervi, Taenia* spp, *Taenia saginata, Baylisascars* spp, *Baylisascaris procyonis, Nematodirus* spp., *Nematordirus battus, Nematodirus helvetianus, Teladorsagia* spp, *Teladorsagia circumcincta.*

In another embodiment of the invention asafoetida or a preparation thereof can combat one or more parasites, or parasites that are resistant to a compound that has a parasite expelling effect, against parasites that are not-resistant, where the parasites occur in Filinae and is selected from the group consisting of *Ancylostoma caninum, Ancylostoma* spp., *Ancylostoma tubaefonne, Dipylidium caninum, Dipylidium* spp., *Dirofilaria imitis, Dirofilaria* spp., *Echinococcus multilocularis, Echinococcus* spp., *Fasciola hepatica/gigantic, Hydatigera taeniaeformis, Hydatigera* spp., *Joyeuxiella pasqualei, Joyeuxiella* spp., *Mesocestoides* spp., *Multiceps multiceps, Multiceps* spp., *Taenia pisiformis, Taenia* spp., *Taenia taeniaformis, Toxocara canis, Toxocara cati, Toxascaris leonina, Toxocara* spp., *Trichuris vulpis, Trichuris* spp., *Uncinaria* spp., *Uncinaria stenocephala, Paramphistomum* spp., *Paramphistomum cervi, Taenia* spp, *Taenia saginata, Baylisascars* spp, *Baylisascaris procyonis, Nematodirus* spp., *Nematordirus battus, Nematodirus helvetianus, Teladorsagia* spp, *Teladorsagia circumcincta.*

In another embodiment of the invention asafoetida or a preparation thereof can combat one or more parasites, or parasites that are resistant to a compound that has a parasite expelling effect, against parasites that are not-resistant, where the parasites occur in Canis and which are selected from the group consisting of *Ancylostoma braziliense, Ancylostoma caninum, Ancylostoma* spp., *Ancylostoma tubaeforme, Dipylidium caninum, Dipylidium* spp., *Echinococcus granulosus, Echinococcus* spp., *Fasciola hepatica/gigantic, Giardia* spp., *Joyeuxiella pasqualei, Joyeuxiella* spp., *Mesocestoides* spp., *Multiceps multiceps, Multiceps* spp., *Strongyloides* spp., *Taenia hydatigena, Taenia ovis, Taenia pisiformis, Taenia* spp., *Toxocara canis, Toxocara cati, Toxocara* spp., *Toxascaris leonina, Toxascaris* spp., *Trichuris vulpis, Trichuris* spp., *Uncinaria* spp., *Uncinaria stenocephala, Paramphistomum* spp., *Paramphistomum cervi, Taenia* spp, *Taenia saginata, Baylisascars* spp, *Baylisascaris procyonis, Nematodirus* spp., *Nematordirus battus, Nematodirus helvetianus, Teladorsagia* spp, *Teladorsagia circumcincta.*

In another embodiment of the invention asafoetida or a preparation thereof can combat one or more parasites, or parasites that are resistant to a compound that has a parasite expelling effect, against parasites that are not-resistant, where the parasites occur in Bovinae and is selected from the group consisting of *Bunostomum phlebotomum, Bunostomum* spp., *Capillaria* spp., *Chabertia* spp., *Chrysoma bezzania, Chrysoma* spp., *Cooperia oncophora, Cooperia pectinata, Cooperia punctata, Cooperia* spp., *Cooperia surnababa, Dictiocaulus* spp., *Dictiocaulus viviparous, Fasciola hepatica/gigantic, Haemonchus placei, Haemonchus* spp., *Hypoderma bovis, Hypoderma lineatum, Hypoderma* spp., *Mecistocirrus digitatus, Mecistocirrus* spp., *Moniezia* spp., *Nematodirus helvetiana, Nematodirus spathiger, Nematodirus* spp., *Oesophagostomum radiatum, Oesophagostomum* spp., *Oesophagostomum venulosum, Ostertagia lyrata, Ostertagia ostertagi, Ostertagia* spp., *Parafilaria* spp., *Strongyloides papillosus, Strongyloides* spp., *Thelazia* spp., *Toxocara vitulorum, Toxocara* spp., *Trichostrongylus axei, Trichostrongylus colubriformis, Trichostrongylus* spp., *Trichostrongylus vitrinus, Trichuris* spp, *Paramphistomum* spp., *Paramphistomum cervi, Taenia* spp, *Taenia saginata,*

*Baylisascars* spp, *Baylisascaris procyonis*, *Nematodirus* spp., *Nematordirus battus*, *Nematodirus helvetianus*, *Teladorsagia* spp, *Teladorsagia circumcincta*.

In another embodiment of the invention asafoetida or a preparation thereof can combat one or more parasites, or parasites that are resistant to a compound that has a parasite expelling effect, against parasites that are not-resistant, where the parasites occur in Capra and *Ovis* and is selected from the group consisting of *Bunostomum phlebotomum*, *Bunostomum* spp., *Capillaria* spp., *Cestodes* (tapeworm), *Chabertia ovina*, *Chabertia* spp., *Cooperia curtecei*, *Cooperia* spp., *Dictiocaulus havoc*, *filarial*, *Dictiocaulus* spp., *Fasciola hepatica/gigantic*, *Gaigeria pachyscelis*, *Gaigeria* spp., *Haemonchus contortus*, *Haemonchus* spp., *Moniezia* spp., *Nematodirus fillicollis*, *Nematodirus spathiger*, *Nematodirus* spp., *Oesophagostomum columbianum*, *Oesophagostomum* spp., *Oesophagostomum venulosum*, *Oestrus ovis*, *Oestrus* spp., *Ostertagia circumcincta*, *Ostertagia* spp., *Ostertagia trifurcate*, *Protostrongylus refuscens*, *Protostrongylus* spp., *Strongyloides papillosus*, *Strongyloides* spp., *Trichostrongylus axei*, *Trichostrongylus colubriformis*, *Trichostrongylus* spp., *Trichostrongylus vitrinus*, *Trichuris ovis*, *Trichuris* spp, *Paramphistomum* spp., *Paramphistomum cervi*, *Taenia* spp, *Taenia saginata*,

*Baylisascars* spp, *Baylisascaris procyonis*, *Nematodirus* spp., *Nematordirus battus*, *Nematodirus helvetianus*, *Teladorsagia* spp, *Teladorsagia circumcincta*, *Toxocara*.

In another embodiment of the invention asafoetida or a preparation thereof can combat one or more parasites, or parasites that are resistant to a compound that has a parasite expelling effect, against parasites that are not-resistant, where the parasites occur in Suidae and is selected form the group consisting of *Ascaris suum*, *Ascaris* spp., *Fasciola hepatica/gigantic*, *Hyostrongylus rubidus*, *Hyostrongylus* spp., *Metastrongylus* spp., *Oesophagostomum* spp., *Stephanuris dentatus*, *Stephanuris* spp., *Strongyloides ransomi*, *Strongyloides* spp., *Trichuris suis*, *Trichuris* spp *Paramphistomum* spp., *Paramphistomum cervi*, *Taenia* spp, *Taenia saginata*, *Baylisascars* spp, *Baylisascaris procyonis*, *Nematodirus* spp., *Nematordirus battus*, *Nematodirus helvetianus*, *Teladorsagia* spp, *Teladorsagia circumcincta*, *Isospora suis*.

In another embodiment of the invention asafoetida or a preparation thereof can combat one or more parasites, or parasites that are resistant to a compound that has a parasite expelling effect, against parasites that are not-resistant, where the parasites occur in human beings and are selected form the group consisting of *Ascaris lumbricoides*, *Ascaris* spp., *Ancylostoma duodenale*, *Ancylostoma* spp., *Echinococcus* spp., *Brugia* spp., *Clonorchis* spp., *Diphyllobothrium latum*, *Diphyllobothrium* spp., *Enterobius vermicularis*, *Enterobius* spp., *Echinococcus granulosus*, *Echinocuccus mulitcularis*, *Echinococcus* spp., *Fasciolopsis buski*, *Fasciolopsis* spp., *Hymenolepsis nana*, *Hymenolepsis* spp., *Necator americanus*, *Necator* spp., *Schistosoma haematobium*, *Schistosoma mansoni*, *Schistosoma japonicum*, *Schistosoma* spp., *Strongyloides stercoralis*, *Strongyloides* spp., *Taenia saginata*, *Taenia solium*, *Taenia* spp., *Trichuris trichiura*, *Trichuris* spp., *Trichinella spiralis*, *Trichinella* spp., *Wucheria* spp., *Fasciola hepatica/gigantic*, *Toxocara canis*, *Toxocara cati*, *Toxascaris leonina*, *Toxocara* spp.

In another embodiment of the invention asafoetida or a preparation thereof can combat one or more parasites, or parasites that are resistant to a compound that has a parasite expelling effect, against parasites that are not-resistant, where the parasites occur in birds and is selected from the group consisting of *Amidostomum anseris*, *Amidostomum* spp., *Ascaridia columbae*, *Ascaridia galli*, *Ascaridia* spp., *Capillaria* spp., *Heterakis gallinarum*, *Heterakis* spp., *Raillietina* spp., *Syngamus trachea*, *Syngamus* spp., *Trichostrongylus* spp. and *Trichostrongylus tenuis*.

In another embodiment of the invention, asafoetida or a preparation thereof is mixed with an animal feed such as milk, cereal mixture, fodders, horse pellets (bix), herbs, hay, fresh grass, predried grass, beet pulp, carrots, apples, seaweed or straw.

In another embodiment of the invention is that wherein asafoetida or a preparation thereof occurs in a composition further comprising a therapeutically acceptable agent or an excipient.

Another embodiment of the invention is the form of administration of a composition according to the invention. Suitable administration forms of asafoetida or preparation of asafoetida for expelling endoparasites are in the form of a paste, powder, form of pill, that are suitable for oral administration; substance suitable for intravenous administration; a suppository; substance suitable for transdermal use such as an ointment or cream. Expelling ectoparasites is preferably by topical administration, whereby asafoetida can be added to the skin, fur, feathers of the animal, or the skin of the person.

In another embodiment of the invention, asafoetida or a preparation of asafoetida is administered at a dose which is sufficient for expelling parasites. The dose is between 0.001 g-0.1 g/kg body weight, and preferably between about 0.05 g-about 0.07 g/kg body weight. Asafoetida is most preferably administered in a quantity about 0.06 g/kg body weight. It is preferably administered at a dose of between about 1 g/5 kg bodyweight and 1 g/100 kg bodyweight. More preferably a dose of between about 1 g/5 kg and about 1 g/50 kg bodyweight, and most preferably about 1 g/15 kg body weight is used.

The table below shows preferred embodiments for the quantity administered in specific animals.

|         | Preferred | Range       |
|---------|-----------|-------------|
| Horse   | 38 g      | 12-60 g     |
| Cow     | 45 g      | 30-60 g     |
| Sheep   | 4 g       | 2-6 g       |
| Goat    | 5 g       | 3-7 g       |
| Pig     | 8 g       | 6-10 g      |
| Dog     | 1 g       | 0.5-4 g     |
| Cat     | 0.3 g     | 0.1-0.7 g   |
| Pigeon  | 0.03 g    | 0.01-0.07 g |
| Chicken | 0.15 g    | 0.03-0.3 g  |

In another embodiment is the use of asafoetida or a preparation thereof for treating mammals and humans infected with *Fasciola Hepatica*, or liver fluke. An infection with liver fluke is known mainly in sheep but also occurs in cattle, horses and even in humans.

In one other embodiment of the invention, Asafoetida or a preparation thereof can be used in combination with already known or still to be developed medicines, phytotherapeutic agents, biocides or food supplements for combating parasites. It is hereby possible for a wider spectrum of parasites to be treated. The active constituents already commercially available as medicine or biocide comprise benzimidazoles such as thiabendazole, mebendazole, fenbendazole, oxibendazole, fenbendazole, oxfendazole, febantel and albendazole; macrocyclic lactones such as ivermectin, abamectin, doramectin, eprinomectin, moxidectin; imidothiazoles such as levamisole, and others such as netobimin, morantel, diethylcarbamazine, niclosamide, praziquantel, pyrantel pamoate, piperazine citrate, flubendazole, piperazine adipate, milbemycin oxime, imidacloprid, emodepside, closantel, oxfendazole, levamisole hydrochloride, or a constituent derived therefrom. Verm-X® and Keep-Well® are already known as food supplement or phytotherapeutic agent.

In another aspect, the invention relates to the use of asafoetida or a preparation thereof as a biocide or a food supplement. A biocide is understood to mean an active substance and/or a preparation which, in the form in which it is supplied to the user, comprises one or more active substances and is intended to destroy, deter, render harmless a harmful organism, to prevent or combat the effects thereof in other manner by chemical and/or biological means. The use of a food supplement means that asafoetida, or a preparation thereof, is mixed with animal feeds for the purpose of expelling or preventing parasites in the animals, or as supplement to normal feed wherein said food supplement is administered as addition.

According to another aspect, the invention relates to a composition of Asafoetida, further comprising a therapeutically acceptable agent or an excipient for the use in a medicine for expelling parasites, more particularly endoparasites such as parasitic worms or helminths and protozoa, from humans, mammals or birds.

Asafoetida is used for expelling or preventing parasites, and animals and people that took the compound, showed less appetite. This can be explained by the correlation between appetite and infection with endoparasites that reside in and infect the small and large intestine causing a deficient nutrient intake through the intestine, and an increased appetite and food intake to compensate the nutrient deficiency. Asafoetida resin expels the endoparasites and this effect results in a new balance in the body whereby sufficient nutrients are absorbed through the intestine. Thereby animals and people have less desire in food/feed intake.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLE

In Vitro Test

*Ascaris suum* and *Ostertagia ostertagi* L3 larvae where cultured on a medium including a concentration range of Asafoetida resin. The efficacy of the product on the viability of the larvae was evaluated, by controlling the motility of the larvae under the microscope, after 24 h and 48 h.

The measured efficacy is the % mortality with regard to the negative controls. The tests were exhibited two times for each species.

Figure 3:
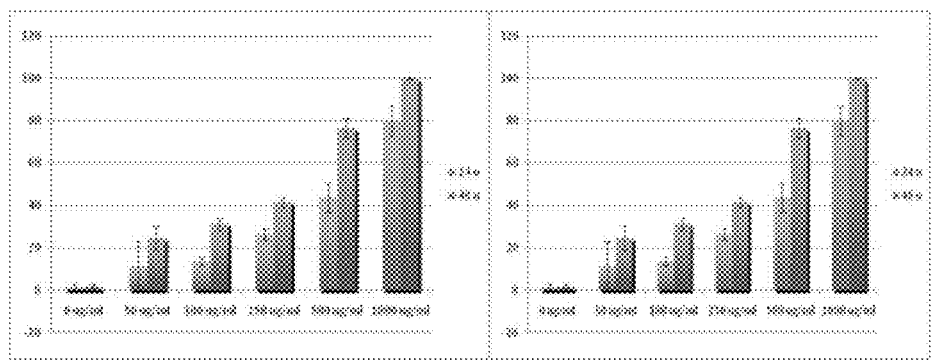
FIG. 3 depicts a $1^{st}$ and $2^{nd}$ Ascaris test.
Figure 4:
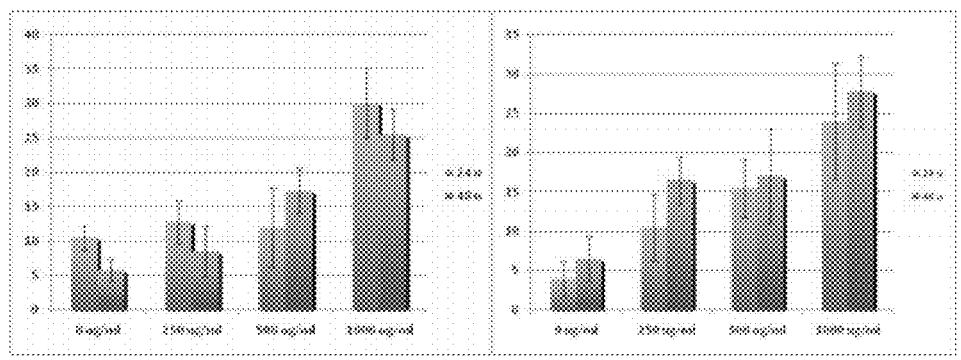
FIG. 4 depicts a 1st and 2nd Ostertagia test.

FIGS. 3 and 4 show the results of the tests. The X-axis shows the concentration of Asafoetida resin that is used. The Y-axis shows the amount of larvae that died. The first chart shows the amount of larvae that died after 24 hours, the second after 48 hours.

Results

*Ascaris suum*: the results of both experiments reveal a dose dependent toxic effect on the helminths. *O. ostertagi*: Both experiments show a doses-dependent toxic effect on the helminths. The highest mortality is found after 48 hours at the highest concentration.

Asafoetida resin has thus an anthelminthic effect for both *Ascaris suum* and *O. ostertagi*. The effect is better for *A. suum* than for *O. ostertagi*. This can be due to the fact that *O. ostertagi* larvae don't feed themselves, and the toxic effect enters the helminths via diffusion, while *A. suum* feed them with the medium.

In Vivo Tests:

Material

The materials used for the experiments below are Asafoetida powder of which the composition is asafoetida powder with Arabic gum and asafoetida resin.

Asafoetida resin is difficult to grate, and is traditionally crushed between stones or with a hammer. The resin used in the experiments was first heated in an oven of 50 degrees so that the resin obtains a soft sticky form. This is then mixed in a blender. The heating of the resin can occur at a temperature of between about 30 and 70 degrees, and is most preferably between about 40 and 60 degrees.

A certain amount of asafoetida resin (about 1 g/15 kg bodyweight) was measured and mixed with apple pulp. The mixture was added to a syringe and orally administered to the animals.

Treatment of Pigs

Coproscopic flotation test of the faeces of two young pigs (average weight in between 135 and 150 kg) revealed an infection with parasites. The pigs were treated once with 10 g of Asafoetida resin mixed with a cereal mixture and milk and after 13 days the faeces where tested again. The table below shows the results of a coproscopic flotation test and the total amount of worm eggs found in the faeces before and after treatment.

TABLE 1

|  | Type of infection before treatment | Amount of worm eggs (EPG)/ oocysts | Type of infection after treatment | Amount of worm eggs/ oocysts |
| --- | --- | --- | --- | --- |
| Pig 1 | *Acaris suum* | 2550 | Neg | Neg |
| Pig 2 | *Isospora suis* | +/−50 oocysts | Neg | Neg |

Treatment of Horses with Asafoetida Powder

Ten horses seriously infected with parasites were treated once with 30 g asafoetida powder in 1 liter of milk, to which a mixture of cereals was optionally added. After ten days a sample of the faeces was taken and sent for a coprological examination. Different methods of analysis are known to the skilled person, including the McMaster method. The presence of different parasites was tested via the McMaster method and the macroscopic examination was negative for all the horses.

One horse was reinfected with *trichostrongylus* spp. after it was moved to another stable. It was then treated once-only with 30 g Asafoetida, mixed with 1 liter of milk and with a cereal mixture. After ten days a faeces sample was taken for a coprological examination. The results of the McMaster method were once again negative.

Treatment of Horses with Asafoetida Resin

One horse (Horse 1) was stabled in a horse-riding centre and had no parasites. The other 70 horses in the horse-riding centre were infected with parasites. It was surprisingly found that horse 1 was the only horse with less appetite compared with the others and required less feed. There is a relation between appetite and infection with endoparasites in horses.

Especially, endoparasites that reside in and infect the small and large intestine of a horse, causes a deficient nutrient intake through the intestine. The horse needs more food and has an increasing appetite.

After certain time, horse 1 got infected, and the faeces were tested. The horse was infected with Strongylidae spp. and had an EPG of 1450 (i.e. 1450 parasite eggs per gram faeces). The horse was also infected with mites. After treating the horse with 38 g asafoetida resin, already after 5 days the coprologic examination revealed EPG of <200 and no more mites were found.

The faeces of two other horses (horse 2 and 3) were also tested. The table below shows the result of the coprologic tests. The coprologic test was performed after about 10 days after treatment with Asafoetida resin.

TABLE 2

|  | Type of infection before treatment | EPG | Type of infection after treatment | EPG |
|---|---|---|---|---|
| Horse 1 | Strongylidae spp. | 1450 | Neg. | <200 |
|  | Mites |  | Neg. |  |
| Horse 2 | Strongylidae spp. | 450 | Neg | <200 |
| Horse 3 | Strongylidae spp. | 800 | Neg | <200 |

Treatment of Horse 4

Figure 2A:
FIGS. 2A-2B depict the effect of Asafoetida resin on an infected horse. Horse 4 was severely infected with parasites. Several treatments with ivermectine, pyrantel, praziquantel and moxidectine, had no result. Apparently, horse 4 was infected with helminths that were resistant to the above anthelmiths (see FIG. 2A). Additionally, the horse suffered from the side effects caused by the anthelmintics. Horse 4 was treated with 38 g Asafoetida powder with Arabic gum mixed in milk and with cereal. Already after 10 days, the first signs of healing were seen; the skin and fur of the horse looked healthier. The horse was cured and gained more than 150 kg in weight within two months (see FIG. 2B).

Horse 4 was severely infected with parasites. Several treatments with ivermectine, pyrantel, praziquantel and moxidectine, had no result. Apparently, horse 4 was infected with helminths that were resistant to the above anthelmiths (see FIG. 2A). Additionally, the horse suffered from the side effects caused by the anthelmintics.

Figure 2B:
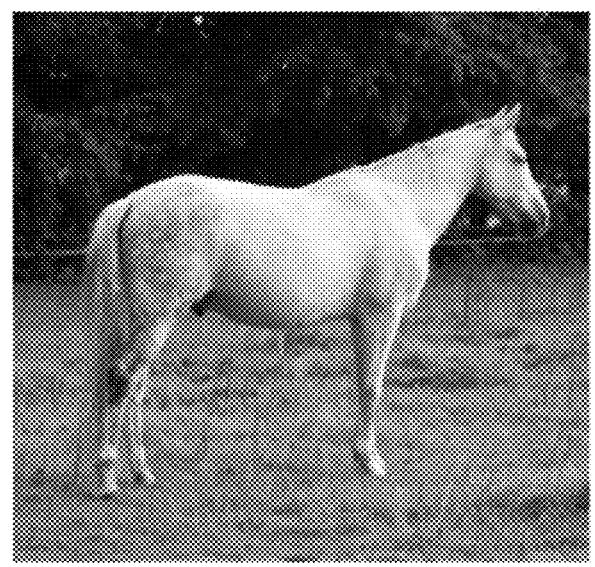

Horse 4 was treated with 38 g Asafoetida powder with Arabic gum mixed in milk and with cereal. Already after 10 days, the first signs of healing were seen; the skin and fur of the horse looked healthier. The horse got cured and gained more than 150 kg in weight within two months (see FIG. 2B).

Treatment of Pets

Figure 1B:

One cat (see FIG. 1A) was infected with parasites. After treating the cat with 0.3 g asafoetida resin, the cat gained weight and lost its parasites (see FIG. 1B).

Three dogs were infected with parasites before treatment. These dogs were treated according to their weight (1 g asafoetida resin in a capsule per 15 kg. weight).

The table below shows the result of a coprological test before treatment and one week after treatment.

TABLE 3

|  | Type of infection before treatment | EPG | Type of infection after treatment | EPG |
|---|---|---|---|---|
| Dog 1 | Toxocara canis | 10 | Neg. | 0 |
| Dog 2 | Toxocara canis | 06 | Neg. | 0 |
| Dog 3 | Toxocara canis | 08 | Neg. | 0 |

Treatment of Cows

Eight cows were infected with parasites before treatment. Four of these cows (Cow 1-4) were treated according to their weight (1 g asafoetida resin in a capsule per 15 kg. weight). Cow 5-8 are a control group and were not treated.

The table below shows the result of a coprological test before treatment and one week after treatment.

TABLE 4

|  | Type of infection before treatment | Amount of eggs/oocysts | Type of infection after treatment | EPG/oocysts |
|---|---|---|---|---|
| Cow 1 | Strongylidae spp. | 50 worm eggs | Strongylidae spp. | <50 |
|  | Eimeria spp. non pathogenous | 50 oocysts | Eimeria spp. non pathogenous | Neg. |
| Cow 2 | Strongylidae spp. | <50 wormig | Strongylidae spp. | <50 |
|  | Eimeria spp. non pathogenous | 100 oocysts | Eimeria ssp. non pathogenous | 50 |
| Cow 3 | Strongylidae spp. | 250 wormig | Strongylidae spp. | 50 |
|  | Eimeria spp. non pathogenous | 50 oocysts | Eimeria ssp. non pathogenous | <50 |
| Cow 4 | Strongylidae spp. | 250 wormig | Strongylidae spp. | <50 |
|  | Eimeria spp. non pathogenous | 50 oocysts | Eimeria ssp. non pathogenous | Neg. |
|  | Nematodirus spp. |  | Nematodirus spp. | Neg. |
| Cow 5 | Strongylidae spp. | 250 wormig | Strongylidae spp. | 250 |
|  | Eimeria spp. non pathogenous |  | Eimeria ssp. non pathogenous | Pos. |
| Cow 6 | Strongylidae spp. | 50 wormig | Strongylidae spp. | 150 |
|  | Eimeria spp. non pathogenous | 150 oocysts | Eimeria ssp. non pathogenous | 150 |
|  | Nematodirus spp. |  | Nematodirus spp. | Pos. |
| Cow 7 | Strongylidae spp. | 50 oocysts | Strongylidae spp. | 50 |
|  | Eimeria spp. non pathogenous | 100 oocysts | Eimeria ssp. non pathogenous | 100 |
|  | Nematodirus spp. |  | Nematodirus spp. | Pos. |
| Cow 8 | Strongylidae spp. | 50 wormig | Strongylidae spp. | 100 |
|  | Eimeria spp. non pathogenous | 150 oocysts | Eimeria ssp. non pathogenous | 150 |
|  | Nematodirus spp. |  | Nematodirus spp. | Pos. |

Human Treatment

One person was infected with Toxocara worms, which she most likely obtained from an infected puppy dog that passed the worm to the person. The person got eye damage in one eye due to ocular larva migration.

The person was treated with 4 g of Asafoetida resin, and had after 2 days less appetite. This can be explained by the correlation between appetite and infection with endoparasites that reside in and infect the small and large intestine causing a deficient nutrient intake through the intestine, and an increased appetite and food intake to compensate the nutrient deficiency. Asafoetida resin expels the endoparasites and this effect results in a new balance in the body whereby sufficient nutrients are absorbed through the intestine. The person had less desire to eat and the duration of feeling of satiation was much longer than before the intake of Asafoetida resin.

Topical Treatment of Pigeons

Eight pigeons were infected with ectoparasites. Five of them had lice (Columbicola columbae), three of them had feather mites (Neoknemidocoptes) on or underneath their feathers and their wings. Such type of infection in pigeons is visible.

A liquid preparation of Asafoetida resin was made by adding 8 g of Asafoetida to 80 ml water. Three pigeons infected with lice and two pigeons infected with lice were treated by adding one drop of the liquid preparation on the neck of the pigeons, and one drop of the liquid preparation under each wing, using a pipette. The pigeons were not washed after the treatment. Three pigeons were not treated.

After 48 hours, the feathers and wings were checked by a person skilled in the art. The five treated pigeons were no longer infected with lice and mites. The three pigeons that had not been treated were still infected: 2 with lice and 1 with mites in their feathers and underneath their wings.

The invention is further described by the following numbered paragraphs:

1. *Ferula assafoetida* (asafoetida) for use in expelling parasites, wherein the parasites are endoparasites in domestic animals, Equus or Suidae; human digestive tract endoparasites; or ectoparasites in humans, mammals or birds.

2. *Ferula assafoetida* (asafoetida) according to paragraph 1, wherein asafoetida is in the form of a preparation and wherein the preparation is preferably a resin derived from asafoetida.

3. *Ferula assafoetida* (asafoetida) of paragraph 1 or 2, wherein the parasites are resistant to a substance that expels parasites that are not-resistant, wherein the substance comprises benzimidazoles, macrocyclic lactones, imidothiazoles, or is selected from the group consisting of thiabendazole, mebendazole, fenbendazole, oxibendazole, oxfendazole, febantel, albendazole, ivermectin, abamectin, doramectin, eprinomectin, moxidectin, levamisole, netobimin, morantel, diethylcarbamazine, niclosamide, praziquantel, pyrantel pamoate, piperazine citrate, flubendazole, piperazine adipate, milbemycin oxime, imidacloprid, emodepside, closantel, levamisole hydrochloride, or a constituent derived there from.

4. *Ferula assafoetida* of any one of the paragraphs 1-3, wherein the mammals are selected form the group consisting of Bovinae, and more particularly Bovinae *Bos; Ovis* and more particularly *Ovis aries*; Capra and more particularly Capra *aegagrus hircus*; Suidae and more particularly suinae *sus*; Canis, and more particularly Canis *lupus familiaris*; Filinae and more particularly *Felis catus*; Equus and more particularly Equus *ferus caballus*; Leporidae and more particularly *Oryctolagus cuniculus*; Cricetidae and more particularly *Cricetus cricetus; Caviidae Cavia*.

5. *Ferula assafoetida* of any one of the paragraphs 1-4, wherein the birds belong to Ava and are selected from the group consisting of poultry, Columbidae, exotic birds and cage-birds including *Psittaciformes, Serinus canaria*, Fringillidae, pheasants, quails, tragopans, partridges, peacocks, guinea fowl, francolins.

6. *Ferula assafoetida* of any one of the paragraphs 1-5, wherein the parasites are selected from the group consisting of endoparasites, comprising tapeworms, roundworms, mine worms, gastrointestinal nematodes, lungworms, flatworms, trematodes, arthropods larvae, liver fluke or coccidia parasites; protozoa, comprising *Cryptosporidium parvum, Eimeria, Giardia duodenalis, Histomonas meleagridis, Neospora caninum, Toxoplasma gondii* and ectoparasites comprising mites, tics, lice, fleas.

7. *Ferula assafoetida* of any one of the paragraphs 1-6, wherein the parasites occur in Equus or are selected from one or more parasites from the group consisting of *Anaplocephala perfoliata, Anaplocephala* spp., *Ascaris* spp., *Cilicodontophorus bicornatus, Cilicodontophorus* spp., *Cilicostephanus asymetricus, Cilicostephanus bidentatus, Cilicostephanus calicatus, Cilicostephanus goldi, Cilicostephanus longibursatus, Cilicostephanus minutes, Cilicostephanus* spp., *Coronocyclus coronatus, Coronocyclus labiatus, Coronocyclus labratus, Coronocyclus* spp., *Craterostomum acuticaudatum, Craterostomum* spp., *Cyathostomum catinatum, Cyathostomum pateratum, Cyathostomum* spp., *Cylicocereus* spp., *Cylicocyclus ashworthi, Cylicocyclus brevicapsulatus, Cylicocyclus elongates, Cylicocyclus insigne, Cylicocyclus leptostomum, Cylicocyclus nassatus, Cylicocyclus radiates, Cylicocyclus* spp., *Cylicocyclus ultrajentinus, Cylicodontophorus bicoronatus, Cylicodontophorus* spp., *Cylicostephanus* spp., *Dictyocaulus amfieldi, Dictyocaulus* spp., *Fasciola hepatica/gigantic, Gasterophilus intestinalis, Gasterophilus nasalis, Gasterophilus* spp., *Gyalocephalus capitatus, Gyalocephalus* spp., *Habronema muscae, Habronema* spp., *Onchocerca* spp., *Onchocerca cervicalis, Oxyuris equi, Oxyuris* spp., *Paranoplocephala mamillana, Paranoplocephala* spp., *Parapoteriostomum mettami, Parapoteriostomum* spp., *Parascaris equorum, Parascaris viviparum, Parascaris* spp., *Petrovinema poculatus, Petrovinema* spp., *Poteriostomum imparidentatum, Poteriostomum* spp., *Strongylus edentates, Strongyloides westeri, Strongylus craterostomum, Strongyloides* spp., *Strongylus edentatus, Strongylus equinus, Strongylus* spp., *Strongylus triodontophorus, Strongylus vulgaris, Trichonema* spp., *Trichostrongylus axei, Trichostrongylus* spp., *Triodontophorus brevicauda, Triodontophorus serratus, Triodontophorus* spp. or *Triodontophorus tenuicollis, Paramphistomum* spp., *Paramphistomum cervi, Taenia* spp, *Taenia saginata, Baylisascars* spp, *Baylisascaris procyonis, Nematodirus* spp., *Nematordirus battus, Nematodirus helvetianus, Teladorsagia* spp, *Teladorsagia circumcincta*.

8. *Ferula assafoetida* of any one of the paragraphs 1-7, wherein the parasites occur in Filinae or are selected from the group consisting of *Ancylostoma caninum, Ancylostoma* spp., *Ancylostoma tubaeforme, Dipylidium caninum, Dipylidium* spp., *Dirofilaria imitis, Dirofilaria* spp., *Echinococcus multilocularis, Echinococcus* spp., *Fasciola hepatica/gigantic, Hydatigera taeniaeformis, Hydatigera* spp., *Joyeuxiella pasqualei, Joyeuxiella* spp., *Mesocestoides* spp., *Multiceps multiceps, Multiceps* spp., *Taenia pisiformis, Taenia* spp., *Taenia taeniaformis, Toxocara canis, Toxocara cati, Toxascaris leonina, Toxocara* spp., *Trichuris vulpis, Trichuris* spp., *Uncinaria* spp. or *Uncinaria stenocephala, Paramphistomum* spp., *Paramphistomum cervi, Taenia* spp, *Taenia saginata, Baylisascars* spp, *Baylisascaris procyonis, Nematodirus* spp., *Nematordirus battus, Nematodirus helvetianus, Teladorsagia* spp, *Teladorsagia circumcincta*.

9. *Ferula assafoetida* of any one of the paragraphs 1-8, wherein the parasites occur in Canis or are selected from the group consisting of *Ancylostoma braziliense, Ancylostoma caninum, Ancylostoma* spp., *Ancylostoma tubaeforme, Dipylidium caninum, Dipylidium* spp., *Echinococcus granulosus, Echinococcus* spp., *Fasciola hepatica/gigantic, Giardia* spp., *Joyeuxiella pasqualei, Joyeuxiella* spp., *Mesocestoides* spp., *Multiceps multiceps, Multiceps* spp., *Strongyloides* spp., *Taenia hydatigena, Taenia ovis, Taenia pisiformis, Taenia* spp.,

*Toxocara canis, Toxocara cati, Toxocara* spp., *Toxascaris leonina, Toxascaris* spp., *Trichuris vulpis, Trichuris* spp., *Uncinaria* spp. or *Uncinaria stenocephala, Paramphistomum* spp., *Paramphistomum cervi, Taenia* spp, *Taenia saginata, Baylisascars* spp, *Baylisascaris procyonis, Nematodirus* spp., *Nematordirus battus, Nematodirus helvetianus, Teladorsagia* spp, *Teladorsagia circumcincta.*

10. *Ferula assafoetida* of any one of the paragraphs 1-9, wherein the parasites occur in Bovinae or are selected from the group consisting of *Bunostomum phlebotomum, Bunostomum* spp., *Capillaria* spp., *Chabertia* spp., *Chrysoma bezzania, Chrysoma* spp., *Cooperia oncophora, Cooperia pectinata, Cooperia punctata, Cooperia* spp., *Cooperia surnababa, Dictiocaulus* spp., *Dictiocaulus viviparous, Fasciola hepatica/gigantic, Haemonchus placei, Haemonchus* spp., *Hypoderma bovis, Hypoderma lineatum, Hypoderma* spp., *Mecistocirrus digitatus, Mecistocirrus* spp., *Moniezia* spp., *Nematodirus helvetiana, Nematodirus spathiger, Nematodirus* spp., *Oesophagostomum radiatum, Oesophagostomum* spp., *Oesophagostomum venulosum, Ostertagia lyrata, Ostertagia ostertagi, Ostertagia* spp., *Parafilaria* spp., *Strongyloides papillosus, Strongyloides* spp., *Thelazia* spp., *Toxocara vitulorum, Toxocara* spp., *Trichostrongylus axei, Trichostrongylus colubriformis, Trichostrongylus* spp., *Trichostrongylus vitrinus* or *Trichuris* spp, *Paramphistomum* spp., *Paramphistomum cervi, Taenia* spp, *Taenia saginata, Baylisascars* spp, *Baylisascaris procyonis, Nematodirus* spp., *Nematordirus battus, Nematodirus helvetianus, Teladorsagia* spp, *Teladorsagia circumcincta.*

11. *Ferula assafoetida* of any one of the paragraphs 1-10, wherein the parasites occur in Capra and *Ovis* or are selected from the group consisting of *Bunostomum phlebotomum, Bunostomum* spp., *Capillaria* spp., *Cestodes* (tapeworm), *Chabertia ovina, Chabertia* spp., *Cooperia curtecei, Cooperia* spp., *Dictiocaulus filarial, Dictiocaulus* spp., *Fasciola hepatica/gigantic, Gaigeria pachyscelis, Gaigeria* spp., *Haemonchus contortus, Haemonchus* spp., *Moniezia* spp., *Nematodirus fillicollis, Nematodirus spathiger, Nematodirus* spp., *Oesophagostomum columbianum, Oesophagostomum* spp., *Oesophagostomum venulosum, Oestrus ovis, Oestrus* spp., *Ostertagia circumcincta, Ostertagia* spp., *Ostertagia trifurcate, Protostrongylus refuscens, Protostrongylus* spp., *Strongyloides papillosus, Strongyloides* spp., *Trichostrongylus axei, Trichostrongylus colubriformis, Trichostrongylus* spp., *Trichostrongylus vitrinus, Trichuris ovis, Trichuris* spp, *Paramphistomum* spp., *Paramphistomum cervi, Taenia* spp, *Taenia saginata, Baylisascars* spp, *Baylisascaris procyonis, Nematodirus* spp., *Nematordirus battus, Nematodirus helvetianus, Teladorsagia* spp, *Teladorsagia circumcincta.*

12. *Ferula assafoetida* of any one of the paragraphs 1-11, wherein the parasites occur in Suidae or are selected from the group consisting of *Ascaris suum, Isospora suis, Ascaris* spp., *Fasciola hepatica/gigantic, Hyostrongylus rubidus, Hyostrongylus* spp., *Metastrongylus* spp., *Oesophagostomum* spp., *Stephanuris dentatus, Stephanuris* spp., *Strongyloides ransomi, Strongyloides* spp., *Trichuris suis* or *Trichuris* spp, *Paramphistomum* spp., *Paramphistomum cervi, Taenia* spp, *Taenia saginata, Baylisascars* spp, *Baylisascaris procyonis, Nematodirus* spp., *Nematordirus battus, Nematodirus helvetianus, Teladorsagia* spp, *Teladorsagia circumcincta.*

13. *Ferula assafoetida* of any one of the paragraphs 1-12, wherein the parasites occur in humans or are selected from the group consisting of *Ascaris lumbricoides, Ascaris* spp., *Ancylostoma duodenale, Echinococcus* spp., *Brugia* spp., *Clonorchis* spp., *Diphyllobothrium latum, Diphyllobothrium* spp., *Enterobius vermicularis, Enterobius* spp., *Echinococcus granulosus, Echinocuccus mulitcularis, Echinococcus* spp., *Fasciolopsis buski, Fasciolopsis* spp., *Hymenolepsis nana, Hymenolepsis* spp., *Necator americanus, Necator* spp., *Schistosoma haematobium, Schistosoma mansoni, Schistosoma japonicum, Schistosoma* spp., *Strongyloides stercoralis, Strongyloides* spp., *Taenia saginata, Taenia solium, Taenia* spp., *Toxocara canis, Toxocara cati, Toxocara* spp., *Trichuris trichiura, Trichuris* spp., *Trichinella spiralis, Trichinella* spp., *Wucheria* spp. or *Fasciola hepatica/gigantic.*

14. *Ferula assafoetida* of any one of the paragraphs 1-13, wherein the parasites occur in Ava or are selected from the group consisting of *Amidostomum anseris, Amidostomum* spp., *Ascaridia columbae, Ascaridia galli, Ascaridia* spp., *Capillaria* spp., *Heterakis gallinarum, Heterakis* spp., *Raillietina* spp., *Syngamus trachea, Syngamus* spp., *Trichostrongylus* spp. or *Trichostrongylus tenuis.*

15. *Ferula assafoetida* of any one of the paragraphs 1-14, wherein *Ferula assafoetida* or the preparation occurs in a composition comprising another active constituent for expelling parasites.

16. *Ferula assafoetida* of any of the paragraphs 1-15, wherein *Ferula assafoetida* or the preparation occurs in a composition taking the form of animal feed.

17. *Ferula assafoetida* of any of the paragraphs 1-16, wherein *Ferula assafoetida* occurs in a composition taking the form of a substance suitable for intravenous administration; suppository, a paste, a powder, a form of pill, or a substance suitable for enteral administration, or a substance suitable for transdermal administration.

18. *Ferula assafoetida* of any one of the paragraphs 1-17, wherein *Ferula assafoetida* occurs in a composition taking the form of a spray, lotion, solution, or other substance suitable for topical use.

19. *Ferula assafoetida* of any one of the paragraphs 1-18, wherein *Ferula assafoetida* is administered at a dose which is sufficient for expelling parasites and is between 0.001 g-0.1 g/kg body weight, preferably between about 0.05 g-about 0.07 g/kg body weight, and most preferably about 0.06 g/kg body weight.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for expelling helminthes resistant to a chemical anthelminthic in an animal in need thereof, comprising the steps of:
   determining whether the animal is infected with a helminth that is resistant to a chemical anthelminthic; and
   administering a composition comprising a therapeutically effective amount of asafoetida obtained from *Ferula asafoetida* to said animal in need thereof.

2. The method according to claim 1, wherein the helminth are resistant to imidothiazole, benzimidazole and macrocyclic lactones.

3. The method according to claim 1, wherein the helminth are resistant to thiabendazole, mebendazole, fenbendazole, oxibendazole, oxfendazole, febantel, albendazole, ivermectin, abamectin, doramectin, eprinomectin, moxidectin, levamisole, netobimin, morantel, diethylcarbamazine, niclosamide, praziquantel, pyrantel pamoate, piperazine citrate, flubendazole, piperazine adipate, milbemycin oxime, imidacloprid, emodepside, closantel or levamisole hydrochloride.

4. The method according to claim 1, wherein said animal is a human, mammal or bird.

5. The method of claim 4, wherein the mammal are selected form the group consisting of Bovinae, *Ovis*, Capra, Suidae, Canis, Filinae, Equus, Leporidae, Cricetidae and *Caviidae Cavia*.

6. The method of claim 4, wherein the mammal are selected form the group consisting of Bovinae *Bos, Ovis aries*, Capra *aegagrus hircus*, suinae *sus*, Canis *lupus familiaris, Felis catus*, Equus *ferus caballus, Oryctolagus cuniculus* and *Cricetus cricetus*.

7. The method of claim 4, wherein the bird belong to Ava.

8. The method of claim 4, wherein the bird are selected from the group consisting of poultry, Columbidae, exotic birds, cage-birds, pheasants, quails, tragopans, partridges, peacocks, guinea fowl and francolins.

9. The method of claim 4, wherein the bird are selected from the group consisting of *Psittaciformes, Serinus canaria* and Fringillidae.

10. The method of claim 1, wherein the helminth are selected from the group consisting tapeworms, roundworms, mine worms, gastrointestinal nematodes, lungworms, flatworms, trematodes, arthropods larvae, liver fluke or coccidian.

11. The method of claim 1, wherein the helminth occur in Equus and are selected from the group consisting of *Anaplocephala perfoliata, Anaplocephala* spp., *Ascaris* spp., *Cilicodontophorus bicornatus, Cilicodontophorus* spp., *Cilicostephanus asymetricus, Cilicostephanus bidentatus, Cilicostephanus calicatus, Cilicostephanus goldi, Cilicostephanus longibursatus, Cilicostephanus minutes, Cilicostephanus* spp., *Coronocyclus coronatus, Coronocyclus labiatus, Coronocyclus labratus, Coronocyclus* spp., *Craterostomum acuticaudatum, Craterostomum* spp., *Cyathostomum catinatum, Cyathostomum pateratum, Cyathostomum* spp., *Cylicocereus* spp., *Cylicocyclus ashworthi, Cylicocyclus brevicapsulatus, Cylicocyclus elongates, Cylicocyclus insigne, Cylicocyclus leptostomum, Cylicocyclus nassatus, Cylicocyclus radiates, Cylicocyclus* spp., *Cylicocyclus ultrajentinus, Cylicodontophorus bicoronatus, Cylicodontophorus* spp., *Cylicostephanus* spp., *Dictyocaulus arnfieldi, Dictyocaulus* spp., *Fasciola hepatica/gigantic, Gasterophilus intestinalis, Gasterophilus nasalis, Gasterophilus* spp., *Gyalocephalus capitatus, Gyalocephalus* spp., *Habronema muscae, Habronema* spp., *Onchocerca* spp., *Onchocerca cervicalis, Oxyuris equi, Oxyuris* spp., *Paranoplocephala mamillana, Paranoplocephala* spp., *Parapoteriostomum mettami, Parapoteriostomum* spp., *Parascaris equorum, Parascaris viviparum, Parascaris* spp., *Petrovinema poculatus, Petrovinema* spp., *Poteriostomum imparidentatum, Poteriostomum* spp., *Strongylus edentates, Strongyloides westeri, Strongylus craterostomum, Strongyloides* spp., *Strongylus edentatus, Strongylus equinus, Strongylus* spp., *Strongylus triodontophorus, Strongylus vulgaris, Trichonema* spp., *Trichostrongylus axei, Trichostrongylus* spp., *Triodontophorus brevicauda, Triodontophorus serratus, Triodontophorus* spp., *Triodontophorus tenuicollis, Paramphistomum* spp., *Paramphistomum cervi, Taenia* spp, *Taenia saginata, Baylisascars* spp, *Baylisascaris procyonis, Nematodirus* spp., *Nematordirus battus, Nematodirus helvetianus, Teladorsagia* spp and *Teladorsagia circumcincta*.

12. The method of claim 1, wherein the helminth occur in Filinae and are selected from the group consisting of *Ancylostoma caninum, Ancylostoma* spp., *Ancylostoma tubaeforme, Dipylidium caninum, Dipylidium* spp., *Dirofilaria imitis, Dirofilaria* spp., *Echinococcus multilocularis, Echinococcus* spp., *Fasciola hepatica/gigantic, Hydatigera taeniaeformis, Hydatigera* spp., *Joyeuxiella pasqualei, Joyeuxiella* spp., *Mesocestoides* spp., *Multiceps multiceps, Multiceps* spp., *Taenia pisiformis, Taenia* spp., *Taenia taeniaformis, Toxocara canis, Toxocara cati, Toxascaris leonina, Toxocara* spp., *Trichuris vulpis, Trichuris* spp., *Uncinaria* spp., *Uncinaria stenocephala, Paramphistomum* spp., *Paramphistomum cervi, Taenia* spp, *Taenia saginata, Baylisascars* spp, *Baylisascaris procyonis, Nematodirus* spp., *Nematordirus battus, Nematodirus helvetianus, Teladorsagia* spp and *Teladorsagia circumcincta*.

13. The method of claim 1, wherein the helminth occur in Canis and are selected from the group consisting of *Ancylostoma braziliense, Ancylostoma caninum, Ancylostoma* spp., *Ancylostoma tubaeforme, Dipylidium caninum, Dipylidium* spp., *Echinococcus granulosus, Echinococcus* spp., *Fasciola hepatica/gigantic, Giardia* spp., *Joyeuxiella pasqualei, Joyeuxiella* spp., *Mesocestoides* spp., *Multiceps multiceps, Multiceps* spp., *Strongyloides* spp., *Taenia hydatigena, Taenia ovis, Taenia pisiformis, Taenia* spp., *Toxocara canis, Toxocara cati, Toxocara* spp., *Toxascaris leonina, Toxascaris* spp., *Trichuris vulpis, Trichuris* spp., *Uncinaria* spp, *Uncinaria stenocephala, Paramphistomum* spp., *Paramphistomum cervi, Taenia* spp, *Taenia saginata, Baylisascars* spp, *Baylisascaris procyonis, Nematodirus* spp., *Nematordirus battus, Nematodirus helvetianus, Teladorsagia* spp and *Teladorsagia circumcincta*.

14. The method of claim 1, wherein the helminth occur in Bovinae and are selected from the group consisting of *Bunostomum phlebotomum, Bunostomum* spp., *Capillaria* spp., *Chabertia* spp., *Chrysoma bezzania, Chrysoma* spp., *Cooperia oncophora, Cooperia pectinata, Cooperia punctata, Cooperia* spp., *Cooperia surnababa, Dictiocaulus* spp., *Dictiocaulus viviparous, Fasciola hepatica/gigantic, Haemonchus placei, Haemonchus* spp., *Hypoderma bovis, Hypoderma lineatum, Hypoderma* spp., *Mecistocirrus digitatus, Mecistocirrus* spp., *Moniezia* spp., *Nematodirus helvetiana, Nematodirus spathiger, Nematodirus* spp., *Oesophagostomum radiatum, Oesophagostomum* spp., *Oesophagostomum venulosum, Ostertagia lyrata, Ostertagia ostertagi, Ostertagia* spp., *Parafilaria* spp., *Strongyloides papillosus, Strongyloides* spp., *Thelazia* spp., *Toxocara vitulorum, Toxocara* spp., *Trichostrongylus axei, Trichostrongylus colubriformis, Trichostrongylus* spp., *Trichostrongylus vitrines, Trichuris* spp, *Paramphistomum* spp., *Paramphistomum cervi, Taenia* spp, *Taenia saginata, Baylisascars* spp, *Baylisascaris procyonis, Nematodirus* spp., *Nematordirus battus, Nematodirus helvetianus, Teladorsagia* spp and *Teladorsagia circumcincta*.

15. The method of claim 1, wherein the helminth occur in Capra or *Ovis* and are selected from the group consisting of *Bunostomum phlebotomum, Bunostomum* spp., *Capillaria* spp., *Cestodes* (tapeworm), *Chabertia ovina, Chabertia* spp., *Cooperia curtecei, Cooperia* spp., *Dictiocaulus filarial, Dictiocaulus* spp., *Fasciola hepatica/gigantic, Gaigeria pachyscelis, Gaigeria* spp., *Haemonchus contortus, Haemonchus* spp., *Moniezia* spp., *Nematodirus fillicollis, Nematodirus spathiger, Nematodirus* spp., *Oesophagostomum columbianum, Oesophagostomum* spp., *Oesophagostomum venulosum, Oestrus ovis, Oestrus* spp., *Ostertagia circumcincta, Ostertagia* spp., *Ostertagia trifurcate, Protostrongylus refuscens, Protostrongylus* spp., *Strongyloides papillosus, Strongyloides* spp., *Trichostrongylus axei, Trichostrongylus colubriformis, Trichostrongylus* spp., *Trichostrongylus vitrinus, Trichuris ovis, Trichuris* spp, *Paramphistomum* spp., *Paramphistomum cervi, Taenia* spp, *Taenia saginata, Baylisascars* spp, *Baylisascaris procyonis, Nematodirus* spp., *Nematordirus battus, Nematodirus helvetianus, Teladorsagia* spp and *Teladorsagia circumcincta*.

16. The method of claim 1, wherein the helminth occur in Suidae and are selected from the group consisting of *Ascaris suum, Isospora suis, Ascaris* spp., *Fasciola hepatica/gigantic, Hyostrongylus rubidus, Hyostrongylus* spp., *Metastrongylus* spp., *Oesophagostomum* spp., *Stephanuris dentatus, Stephanuris* spp., *Strongyloides ransomi, Strongyloides* spp., *Trichuris suis, Trichuris* spp, *Paramphistomum* spp., *Paramphistomum cervi, Taenia* spp, *Taenia saginata, Baylisascars* spp., *Baylisascaris procyonis, Nematodirus* spp., *Nematordirus battus, Nematodirus helvetianus, Teladorsagia* spp and *Teladorsagia circumcincta*.

17. The method of claim 1, wherein the helminth occur in humans and are selected from the group consisting of *Ascaris lumbricoides, Ascaris* spp., *Ancylostoma duodenale, Echinococcus* spp., *Brugia* spp., *Clonorchis* spp., *Diphyllobothrium latum, Diphyllobothrium* spp., *Enterobius vermicularis, Enterobius* spp., *Echinococcus granulosus, Echinocuccus mulitcularis, Echinococcus* spp., *Fasciolopsis buski, Fasciolopsis* spp., *Hymenolepsis nana, Hymenolepsis* spp., *Necator americanus, Necator* spp., *Schistosoma haematobium, Schistosoma mansoni, Schistosoma japonicum, Schistosoma* spp., *Strongyloides stercoralis, Strongyloides* spp., *Taenia saginata, Taenia solium, Taenia* spp., *Toxocara canis, Toxocara cati, Toxocara* spp., *Trichuris trichiura, Trichuris* spp., *Trichinella spiralis, Trichinella* spp., *Wucheria* spp. and *Fasciola hepatica/gigantic*.

18. The method of claim 1, wherein the helminth occur in Ava and are selected from the group consisting of *Amidostomum anseris, Amidostomum* spp., *Ascaridia columbae, Ascaridia galli, Ascaridia* spp., *Capillaria* spp., *Heterakis gallinarum, Heterakis* spp., *Raillietina* spp., *Syngamus trachea, Syngamus* spp., *Trichostrongylus* spp. and *Trichostrongylus tenuis*.

19. The method of claim 1, wherein said composition comprising asafetida further comprise an additional active ingredient for expelling the helminth.

20. The method of claim 1, wherein said composition is in the form of an animal feed.

21. The method of claim 1, wherein said composition is in a form suitable for intravenous administration; a suppository; a paste; a powder; a pill; a form suitable for enteral administration or a form suitable for transdermal administration.

22. The method of claim 1, wherein said composition in the form of a spray, lotion, solution, or other form suitable for topical use.

23. The method of claim 1, wherein said asafoetida is administered at a dose of between 0.001 g to 0.1 g/kg body weight.

24. The method of claim 1, wherein said asafoetida is administered at a dose of between about 0.05 g to about 0.07 g/kg body weight.

25. The method of claim 1, wherein said asafoetida is administered at a dose of about 0.06 g/kg body weight.

* * * * *